(12) United States Patent
Schreurs et al.

(10) Patent No.: US 9,295,190 B2
(45) Date of Patent: Mar. 29, 2016

(54) SEED TREATMENT COMPOSITION

(71) Applicant: DSM IP ASSETS B.V., Heerlen (NL)

(72) Inventors: Frederik Jan Hendrik Schreurs, Maarssen (NL); Jacobus Stark, Echt (NL); Angelique De Rijk, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/365,685

(22) PCT Filed: Dec. 21, 2012

(86) PCT No.: PCT/EP2012/076627
§ 371 (c)(1),
(2) Date: Jun. 16, 2014

(87) PCT Pub. No.: WO2013/092995
PCT Pub. Date: Jun. 27, 2013

(65) Prior Publication Data
US 2014/0309108 A1 Oct. 16, 2014

(30) Foreign Application Priority Data
Dec. 22, 2011 (EP) ..................... 11195253

(51) Int. Cl.
*A01C 1/06* (2006.01)
*A01N 25/08* (2006.01)
*A01N 43/90* (2006.01)

(52) U.S. Cl.
CPC . *A01C 1/06* (2013.01); *A01N 25/08* (2013.01); *A01N 43/90* (2013.01)

(58) Field of Classification Search
None
See application file for complete search history.

(56) References Cited

U.S. PATENT DOCUMENTS

| 4,344,979 A | 8/1982 | Gago et al. |
| 2006/0150489 A1 | 7/2006 | Legro et al. |

FOREIGN PATENT DOCUMENTS

| WO | 2004049778 A1 | 6/2004 |
| WO | 2008009657 A2 | 1/2008 |

OTHER PUBLICATIONS

International Search Report corresponding to PCT/EP2012/076627 mailed Mar. 1, 2013.
Saler, Ramling S., "Pesticifal Effects on Nodulation and N-Fixation in Groundnut (Arachis hypogaea L) C.V.SB-11", 2011 International Conference on Biology, Environment and Chemistry, IPCBEE, vol. 24 (2011), IACSIT Press, Singapore.

*Primary Examiner* — Abigail Fisher
*Assistant Examiner* — Frank Choi
(74) *Attorney, Agent, or Firm* — McBee Moore Woodward & Vanik IP, LLC

(57) ABSTRACT

The present invention relates to novel compositions for treating seeds. Moreover, the present invention is directed to the production of these compositions and the uses of these compositions.

15 Claims, No Drawings

SEED TREATMENT COMPOSITION

CROSS REFERENCE TO RELATED APPLICATIONS

This application is a §371 National Stage Application of PCT/EP2012/076627, filed Dec. 21, 2012, which claims priority to European Application No. EP11195253.7, filed, Dec. 22, 2011, all of which are incorporated by reference in their entireties.

BACKGROUND

1. Field of the Invention

The present invention relates to novel compositions for treating seeds as well as their production and uses.

2. Description of Related Art

The agricultural field produces crops of many varieties such as inter alia legumes, fruits, lettuce, wheat, barley, corn and rice. Many of these crops are grown from seeds that vary in their innate ability to resist physical damage due to unfavourable storage or environmental conditions, all of which affects their subsequent ability to grow into adult plants. Furthermore, seeds are susceptible to damage by plant pathogens including fungi, bacteria, viruses, and nematodes and are vulnerable to insects, birds, rodents, and other organisms that rely on them as a food source. Fungi are one of the most economically important groups of plant pathogens and are responsible for huge annual losses of marketable food, fibre and feed.

To reduce yield losses due to for instance fungal spoilage, a significant fraction of the seeds is currently treated with one or more synthetic agrochemicals. The use of synthetic agrochemicals to control plant pathogens, however, has increased costs to farmers and has caused harmful effects on the ecosystem. Consumers and government regulators alike are becoming increasingly concerned with the environmental hazards associated with the production and use of synthetic agrochemicals for protecting seeds from pathogens.

Furthermore, applying agrochemicals to the seeds themselves is fraught with problems such as bonding of the agrochemicals to the soil, agglomeration of the seeds due to the application of the agrochemicals and the use of expensive and complex chemical application equipment. In addition, seeds can be adversely affected by agrochemicals, as these chemicals can be toxic to the seeds and to the plants that sprout from the seeds. Such toxicity limits the amount of these agrochemicals that can safely be applied to the seeds. One undesirable effect of the toxicity is the reduction of the germination rate and/or speed, or even total lack of germination, of seeds that have been treated. Typically, the germination rate and/or speed of seeds that have been treated with an agrochemical that is toxic decreases with time after the chemical has been applied, thereby limiting the shelf life of the treated seeds. The toxicity of agrochemicals has been dealt with in several ways.

The inclusion of chemicals which ameliorate the toxic effects of agrochemicals along with the seeds is widely used. This solution however requires the application of an additional, often expensive, chemical component to the seeds.

Another way to overcome the toxic effect is to encapsulate the agrochemical in a matrix which limits its movement. This method can limit the contact of the agrochemical with the seeds and the emerging seedlings, while permitting the chemical to become available later during germination and initial plant growth as the chemical is released from the matrix. The proper operation of encapsulation technology depends on careful matching of the physical and chemical properties of the agrochemical and the encapsulating matrix. Neither one matrix, nor one encapsulation process, is suitable for encapsulation of all agrochemicals now in use for seed treatment. Moreover, the encapsulation matrix is susceptible to cracking.

Yet another way to overcome the toxic effect is to cover the seed with a relatively thick layer of inert material onto which the agrochemical is applied in such a way that it is not directly in contact with the seed (see WO 2004/049778). However, a disadvantage of this method is that at high dosage of agrochemical is necessary to be effective which still may lead to a possible toxic effect of the agrochemical for the seeds. Furthermore, due to the high dosage the coating's physiochemical properties may be changed significantly, indirectly producing a negative effect due to a change in the oxygen/water balance in the coating.

A further alternative includes the simultaneous sowing of seed-containing pellets and agrochemical-containing pellets as separate pellets (see US 2006/0150489). A disadvantage of this solution is that two separate pellets need to be made which is cumbersome and expensive. Moreover, this solution can stimulate irregular use of the agrochemical-containing pellets as there is no or only limited control at the application time, rate and location of the pellets.

Thus, there is a significant need for novel coating compositions for the control of seed pathogens that on the one hand possess a lower risk of pollution and environmental hazards than the currently used agrochemicals and that on the other hand are not toxic for the seeds.

SUMMARY

A large part of the damage to crop plants which is caused by phytopathogenic microorganisms occurs as early as when the seeds are attacked during storage and after the seeds are introduced into the soil, during and immediately after germination of the seeds. This phase is particularly critical since the roots and shoots of the growing plants are particularly sensitive and even minor damage can lead to deformation or to the death of the whole plant. It is therefore of particular interest to let the seeds germinate as fast as possible. In accordance with the present invention, it has been discovered that polyene fungicides such as natamycin can be used to improve and fasten germination of seeds.

DETAILED DESCRIPTION OF A PREFERRED EMBODIEMENT

In a first aspect the present invention relates to a method for improving seed germination, said method comprising the step of contacting the seed, the medium to be planted by the seed or both with a polyene fungicide.

The polyene fungicide improves the seed germination by 1 to 15%, preferably 5 to 15% after 14 to 16 days of incubation of the seeds at 20-30° C. In an embodiment the polyene fungicide improves the seed germination by at least 1%, at least 3%, at least 5%, at least 8%, at least 10%, preferably at least 15%, more preferably at least 20% and most preferably at least 25% after 14 to 16 days of incubation of the seeds at 20-30° C. In detail, the seeds were incubated in a professional sterile germination room with set temperatures and light conditions. Seeds were planted in a sterile roll paper according to well known ISTA (International Seed Testing Association) procedures (see Handbook International Rules for Seed Testing, Edition 2011, Chapter 5, published by the International Seed Testing Association, Switzerland). The planted seeds were subjected to the following cycle for 14 to 16 days: 12 hours dark at 20° C. followed by 12 hours of light at 30° C.; humidity was between 98 and 100%.

In an embodiment the polyene fungicide is selected from the group consisting of natamycin, nystatin, amphotericin B, trienin, etruscomycin, filipin, chainin, dermostatin, lymphosarcin, candicidin, aureofungin A, aureofungin B, hamycin A, hamycin B and lucensomycin. In a preferred embodiment the polyene fungicide is natamycin. In an embodiment the seed, medium to be planted by the seed or both may also be contacted by two or more different polyene fungicides. Preferably, one of the polyene fungicides is natamycin. It is to be understood that derivatives of polyene fungicides, such as natamycin, including, but not limited to, salts or solvates of polyene fungicides, such as natamycin, or modified forms of polyene fungicides, such as natamycin, may also be contacted with the seed, medium to be planted by the seed or both. Examples of commercial products containing natamycin are the products with the brand name Delvocid®. Such products are produced by DSM Food Specialties (The Netherlands) and may be solids containing e.g. 50% (w/w) natamycin or liquids comprising between e.g. 0.5-50% (w/v) natamycin. Said commercial products can be contacted with the seed, medium to be planted by the seed or both.

"A medium to be planted by the seed" as used herein means any growing environment suitable for growing a plant and/or seedling from a seed such as soil and other growth media (natural or artificial). The polyene fungicide can be applied to for example the soil in-furrow, growing blocks, gutters or in T-bands. The polyene fungicide can be applied at the same time as the seeds are sown. In an embodiment the polyene fungicide can be applied to the seed, medium to be planted by the seed or both through irrigation water.

"Seed" as used herein means any resting stage of a plant that is physically detached from the vegetative stage of a plant. The term "resting" refers to a state wherein the plant retains viability, within reasonable limits, in spite of the absence of light, water and/or nutrients essential for the vegetative (i.e. non-seed) state. Seeds may be stored for prolonged periods of time and can be used to re-grow another plant individual of the same species. In particular, the term "seed" refers to true seeds, but does not embraces plant propagules such as suckers, corms, bulbs, fruit, tubers, grains, cuttings and cut shoots. In other words, seeds are a ripened ovule of gymnosperms and angiosperm which develops following fertilization and contains an embryo surrounded by a protective cover. Alternatively, artificial seeds do not need fertilization. Other food reserve storing tissues such as e.g. endosperm may be present in mature seeds.

Seeds of plant varieties of all types which are used in agriculture, in greenhouses, in forestry, in garden construction or in vineyards can be contacted with the polyene fungicide. In particular, this concerns seeds of corn, maize, triticale, teff, peanut, canola, rape, poppy, olive, coconut, grasses, cacao, soy, cotton, beet, (e.g. sugar beet and fodder beet), rice (any rice may be used, but is preferably selected from the group consisting of *Oryza sativa* sp. japonica, *Oryza sativa* sp. javanica, *Oryza sativa* sp. indica, and hybrids thereof), sorghum, millet, teff, spelt, wheat, durum wheat, barley, oats, rye, sunflower, sugar cane, turf, pasture, alfalfa, or tobacco. The polyene fungicide can also be used for the treatment of the seeds of fruit plants including, but not limited to, rosaceous fruit, for example apples and pears; stone-fruits, for example peaches, nectarines, cherries, plums and apricots; citrus fruit, for example, oranges, grapefruit, limes, lemons, kumquats, mandarins and satsumas; nuts, for example pistachios, almonds, walnuts, coffee, cacao and pecan nuts; tropical fruits, for example, mango, papaya, pineapple, dates and bananas; and grapes; and vegetables including, but not limited to, leaf vegetables, for example endives, lambs lettuce, rucola, fennel, globe (head lettuce) and loose-leaf salad, chard, spinach and chicory; brassicas, for example, cauliflower, broccoli, Chinese cabbage, kale (winter kale or curly kale), kohlrabi, Brussels sprouts, red cabbage, white cabbage and savoy; fruiting vegetables, for example, aubergines (also called eggplants), cucumbers, paprika, peppers (hot), marrow, tomatoes, courgettes, melons, watermelons, pumpkins and sweet corn; root vegetables, for example celeriac, turnip, carrots, swedes, radishes, horse radish, beetroot, salsify, celery; pulses, for example, peas and beans; and bulb vegetables, for example leeks, garlic and onions. The polyene fungicide can also be used for the treatment of the seeds of ornamental seeds, for example, roses, pansy, impatiens, petunia, begonia, Lisianthus, sunflower, ageratum, chrysanthemum and geranium. In a preferred embodiment, the polyene fungicide is used for the treatment of seeds of tomatoes, cabbages (e.g. Chinese cabbage, kale (winter kale or curly kale), kohlrabi, Brussels sprouts, red cabbage, white cabbage and savoy), onions, paprika, aubergines (also called eggplants), lettuce (e.g. endives, lambs lettuce, rucola, fennel, globe (head lettuce) and loose-leaf salad, chard, spinach and chicory), corn, rice, soy and cucurbitaceae (e.g. cucumbers, pumpkins, watermelons and melons).

The seeds may be transgenic seeds, i.e. seeds of a transgenic plant. As used herein "transgenic plant" means a plant or progeny thereof derived from a transformed plant cell or protoplast, wherein the plant DNA contains an introduced exogenous DNA molecule not originally present in a native, non-transgenic plant of the same strain.

According to the present invention, to improve their germination seeds are treated by applying a polyene fungicide to the seeds. Although the present method can be applied to seeds in any physiological state, it is preferred that the seeds be in a sufficiently durable state that they incur no significant damage during the seed treatment process. Typically, the seeds are seeds that have been harvested from the field; removed from the plant; and/or separated from the fruit and any cob, pod, stalk, outer husk, and surrounding pulp or other non-seed plant material. The seeds are preferably also biologically stable to the extent that the treatment would cause no biological damage to the seeds. In one embodiment, for example, the treatment can be applied to seeds that have been harvested, cleaned and dried to a specific moisture content. In an alternative embodiment, the seeds can be dried and then primed with water and/or another material and then re-dried before, during or after treatment with the polyene fungicide.

The polyene fungicide can be applied "neat", that is, without any diluting or additional components present. However, the polyene fungicide is typically applied to the seeds in the form of a composition and/or coating and/or formulation. Ergo, the composition and/or coating and/or formulation according to the invention may be a (physical) mixture of a polyene fungicide and at least one other component. However, the composition and/or coating and/or formulation may also be any combination of a polyene fungicide and at least one other component, it not being required for the polyene fungicide and the at least one other component to be present together in the same composition and/or coating and/or formulation. An example of a composition and/or coating and/or formulation according to the invention in which the polyene fungicide and the at least one other component are not present together in the same composition and/or coating and/or formulation is a kit of parts. In a kit of parts, two or more components of a kit are packaged separately, i.e. not preformulated. As such, kits include one or more separate containers such as vials, cans, bottles, pouches, bags or canisters, each container containing a separate component for an agrochemical composition. Examples are two-component, three component or even four component kits. The seeds can be contacted with the polyene fungicide using all suitable seed treatment and especially seed dressing techniques known in the art, such as seed coating (e.g. seed pelleting, encrusting, film coating), seed dusting and seed imbibition (e.g. seed soaking, priming). Here, "seed treatment" refers to all methods that bring seeds and the polyene fungicide into contact with each other, and "seed dressing" refers to methods of seed treatment which provide the seeds with an amount of the polyene fungicide, i.e. which generate a seed comprising the polyene fungicide. In principle, the treatment can be applied to the seeds at any time from the harvest of the seeds to the sowing of the seeds. The seeds can be treated immediately before, or during, the planting of the seed. However, the treatment may also be carried out several weeks or months, for example up to 13 months, before planting the seed, for example in the form of a seed dressing treatment. The treatment can be applied to unsown seeds. As used herein, the term "unsown seeds" is meant to include seeds at any period from the harvest of the seeds to the sowing of the seeds in the ground for the purpose of germination and growth of a plant. Seeds can also be treated after sowing by e.g. applying the polyene fungicide to the soil or medium, rather than directly to the seed. However, by applying the treatment to the seeds prior to the sowing of the seeds the operation is simplified. In this manner, seeds can be treated, for example, at a central location and then dispersed for planting. This permits the person who plants the seeds to avoid the handling and use of the polyene fungicide and to merely handle and plant the treated seeds in a manner that is conventional for regular untreated seeds, which reduces human exposure. The seeds to be treated can be primed or unprimed seeds. Priming of seeds is done to bring the seeds to the same germination level under controlled conditions. Examples of priming techniques are osmo priming and drum priming. These priming techniques are known to the skilled artisan.

Usually, a device which is suitable for seed treatment, for example a mixer for solid or solid/liquid components, is employed until the polyene fungicide is distributed uniformly onto the seeds. The polyene fungicide can be applied to seeds by any standard seed treatment methodology, including, but not limited to, mixing in a container (e.g. bottle, bag, tumbler, rotary coater, fluidized bed or sprayer), mechanical application, tumbling, spraying, and immersion. If appropriate, this is followed by drying of the seeds. Spray seed treatment is a method usually used for treating large volume of rice seeds. For this purpose, a solution obtained by dilution of a composition (e.g. a FS, LS, DS, WS, SS and ES) is sprayed continuously on seeds in a spray chamber and then dried at elevated temperature (e.g. 25 to 40° C.) in a drying chamber.

In another embodiment the seeds can be subjected to coating or imbibition (e.g. soaking). "Coating" denotes any process that endows the outer surfaces of the seeds partially or completely with a layer or layers of non-plant material. Coating is most commonly used for broad acre crops like rice, corn and also vegetable seeds. According to this method the seeds are cleaned and afterwards coated with a diluted formulation by using e.g. a rotating pot-mixer for about several minutes and followed by reversible rotation. Afterwards, the seeds are dried.

"Imbibition" refers to any process that results in penetration of the polyene fungicide into the germinable parts of the seed and/or its natural sheath, (inner) husk, hull, shell, pod and/or integument. According to the soaking method, the seeds are cleaned and packed in a bag that is sunk into the equivalent volume of chemical solution with seed volume, wherein the chemical solution normally is obtained by the dilution of a formulation such as FS, LS, DS, WS, SS and ES. Afterwards, the seed are dried. Soaking is most commonly applied for rice seed.

The invention also relates to a treatment of seeds which comprises providing seeds with a coating that comprises a polyene fungicide and to a treatment of seeds which comprises imbibition of the seeds with a polyene fungicide. Coating can also comprise spraying a polyene fungicide onto the seeds, while agitating the seeds in an appropriate piece of equipment such as a tumbler or a pan granulator. Coating can also be carried out by moistening the external surface of the seeds and applying the polyene fungicide to the moistened seeds and drying the obtained seeds. The seeds can be moistened, for example, by spraying with water or an aqueous solution. If the seeds are sensitive to swelling in water, they can be moistened with an aqueous solution containing an anti-swelling agent.

Coating may be applied to the seeds using conventional coating techniques and machines, such as fluidized bed techniques, the roller mill method, rotostatic seed treaters, and drum coaters. Other methods such as the spouted beds technique may also be useful. The seeds may be pre-sized before coating. After coating, the seeds are typically dried and then transferred to a sizing machine for sizing. Drying can be carried out by natural ventilation, but also in accordance with any technique which is in itself known, such as passing an optionally heated, forced stream of air over the seeds, which can be arranged, for this purpose, in apparatuses such as sieves.

When coating seeds on a large scale (for example a commercial scale), seeds may be introduced into treatment equipment (such as a tumbler, a drum, a plate, a mixer or a pan granulator) either by weight or by flow rate. The amount of polyene fungicide that is introduced into the treatment equipment can vary depending on the seed weight to be coated, surface area of the seeds, the concentration of the polyene fungicide, the desired concentration on the finished seeds, and the like. The polyene fungicide can be applied to the seeds by a variety of means, for example by a spray nozzle or revolving disc. The amount of polyene fungicide is typically determined by the required rate of polyene fungicide necessary for efficacy. As the seeds falls into the treatment equipment, the seeds can be treated (for example by misting or spraying with the polyene fungicide) and passed through the treatment equipment under continual movement/tumbling where it can be coated evenly and dried before storage or use. In another embodiment, a known weight of seeds can be introduced into the treatment equipment. A known volume of polyene fungicide can be introduced into the treatment equipment at a rate that allows the polyene fungicide to be applied evenly over the seeds. Powder for the encrusting can be added manually or through an automated powder feeder. During the application, the seeds can be mixed, for example by spinning or tumbling. The seeds can optionally be dried or partially dried during the tumbling operation. After complete coating or encrusting, the treated seeds can be removed to an area for further drying or additional processing, use, or storage. In still another embodiment, seeds can be coated in laboratory size commercial treatment equipment such as a tumbler, a mixer, or a pan granulator by introducing a known weight of seeds in the treatment equipment, adding the desired amount of polyene fungicide, tumbling or spinning the seeds and placing them on a tray to thoroughly dry. In another embodiment, seeds can also be coated by placing the known amount of seeds into a narrow neck bottle or receptacle with a lid. While tumbling, the desired amount of polyene fungicide can be added to the receptacle. The seeds are tumbled until they are coated, encrusted or pelleted with the polyene fungicide. After coating, encrusting or pelleting, the seeds can optionally be dried, for example on a tray. If necessary, drying can be done by conventional methods. For example, a desiccant or mild heat (such as below about 40° C.) may be employed to produce a dry coating or encrusting.

Alternatively, coating may also be done by applying a "sticking agent" such as a filler or binder as an adhesive film over the seeds so that the polyene fungicide in the form of a powder can be bonded to the seeds to form a coating, encrusting or pellet. For example, a quantity of seeds can be mixed with a sticking agent, and optionally agitated to encourage uniform coating of the seeds with the sticking agent. In the second step, the seed coated with the sticking agent can then be mixed with the powdered mixture of polyene fungicide. The dry formulation of the polyene fungicide may contain other components as discussed below. The mixture of seeds and polyene fungicide can be agitated, for example by tumbling, to encourage contact of the sticking agent with the powdered material, thereby causing the powdered material to stick to the seeds.

As already indicated above, the polyene fungicide may be comprised in a composition and/or coating and/or formulation (all denoted as composition hereafter). The composition may comprise one or more further components. The components include, but not limited to, other pesticides (such as fungicides, acaricides, miticides, insecticides, insect repellants, bird repellants, rodenticides, molluscicides, nematicides, bactericides, and fumigants), herbicides, adjuvants, wetters, nutrients, waxes, anti-oxidation agents, gene activators protective colloids, surfactants, minerals, chemical hybridizing agents, pigments, auxins, sticking agents, antibiotics and other drugs, biological attractants, colorants, dispersing agents, solvents, solid carriers, growth regulators, pheromones, thickening agents, dyes, safeners, fertilizers, anti-freeze agents, biocontrol agents (e.g. naturally-occurring or recombinant bacteria and/or fungi), liquid diluents, binders (e.g. to serve as a matrix for the polyene fungicide), fillers (e.g. fine powders of organic or mineral type for protecting the seeds during stress conditions), plasticizers (to improve flexibility, adhesion, and/or spreadability), drying agents, solubilizers, dispersing agents, anti-foaming agents.

The composition that is used to treat the seeds in the present invention can be in the form of a soluble concentrate (SL, LS), a dispersible concentrate (DC), an emulsifiable concentrate (EC), a suspension (SC, OD, FS), an emulsion (EW, EO, ES), a slurry of particles in an aqueous medium (e.g. water), a paste, a water-dispersible or water-soluble powder (WP, SP, SS, WS), a pastille, a water-dispersible or water-soluble granule (WG, SG), a dry granule (GR, FG, GG, MG), a gel formulation (GF), a dustable powder (DP, DS), to name just a few. Water-soluble concentrates (LS), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of seeds. These compositions can be applied to seeds, diluted or undiluted. In a preferred embodiment the composition comprising the polyene fungicide further comprises a filler, a binder or both. In other words, the seeds can be contacted with a composition comprising a polyene fungicide, a filler, and/or a binder. Alternatively, the seeds can also be contacted with the separate components. Contacting can be dome at the same time or separately. For example, the seeds can be contacted with a composition comprising a filler and a polyene fungicide and thereafter with a composition comprising a filler and a binder. Alternative combinations are within the reach of the skilled artisan.

In a preferred embodiment the filler is selected from the group consisting of a carbonate, wood flour, diatomaceous earth and a combination thereof. In a preferred embodiment the filler is a carbonate. Examples of carbonates are calcium carbonate, magnesium carbonate or a combination thereof. In a preferred embodiment the filler is calcium carbonate.

In a preferred embodiment the binder is selected from the group consisting of lignosulphonate, polyvinylpyrrolidone and a combination thereof. Polyvinylpyrrolidone is a water-soluble polymer made from the monomer N-vinylpyrrolidone $((C_6H_9NO)_N)$. The molecular weight depends on the number of monomer units. Lignosulphonate can be added as copper lignosulphonate, zinc lignosulphonate, magnesium lignosulphonate, manganese lignosulphonate, sodium lignosulphonate, calcium lignosulphonate, ammonium lignosulphonate, or a combination thereof.

In general, the amount of polyene fungicide that is applied to the seeds will range from about 10 grams to about 4000 grams of polyene fungicide per 100 kg of seeds. Preferably, the amount of polyene fungicide will be within the range of about 50 grams to about 3000 grams polyene fungicide per 100 kg of seeds, more preferably within the range of about 100 grams to about 2000 grams polyene fungicide per 100 kg of seeds.

Ergo, the present invention also relates to a seed treatment composition comprising a filler, a binder and a polyene fungicide. In an embodiment the polyene fungicide is natamycin. In a further embodiment the filler is calcium carbonate. In another embodiment the binder is lignosulphonate, polyvinylpyrrolidone or a combination thereof.

In an embodiment the polyene fungicide is present in an amount of from 0.05% to 50% of the total weight of the composition. If formulated as a suspension or slurry, the concentration of the polyene fungicide in the composition is preferably 0.05% to 25% of the total weight of the composition, preferably 0.1% to 20% of the total weight of the composition. In general, the proportion of filler can vary within very wide limits. It is generally between 0.1 and 99% of the total weight of the composition and preferably between 0.5% and 99% of the total weight of the composition.

In a further aspect the invention relates to a seed comprising a filler, a binder and a polyene fungicide. In an embodiment the polyene fungicide is natamycin. In an embodiment the seed comprises a seed treatment composition according to the present invention. The seed may be handled, transported, stored and distributed in the manner of seeds that do not comprise these compounds. Likewise, they may be sown and watered in the same manner as seeds that do not comprise these compounds as well, using conventional equipment. Typically, the present invention is applicable to seeds of crops to be grown in soil or transplant pots, although it may be applied to other plants and growing media without departing from the scope of the invention. It has been found that the treatments according to the present invention can impart long-lasting desired effects of the polyene fungicide to the seeds and resulting plants without need for retreatment.

Another aspect of the present invention pertains to a medium for growing a plant comprising a filler, a binder and a polyene fungicide. In an embodiment the polyene fungicide is natamycin. In an embodiment the medium for growing a plant comprises a seed treatment composition according to the present invention.

In yet another aspect the present invention is concerned with a method for growing a plant, said method comprising the steps of a) sowing a seed according to the present invention, sowing a seed into a medium according to the present invention or sowing a seed according to the present invention into a medium according to the present invention, and b) allowing the plant to grow from the seed. The seeds can be sowed manually or mechanically. The plant can be cultivated and brought up according to a usual manner. Obviously, a sufficient amount of water and nutrients needs to be added to achieve growth of the plant.

A further aspect of the present invention relates to the use of a polyene fungicide to improve seed germination. In an embodiment the polyene fungicide is natamycin.

Use of polyene fungicide to improve the development of roots from seedlings is another aspect of the present invention. In an embodiment the polyene fungicide is natamycin. The term "root" as used herein refers to parts of a plant which are normally, in order to fulfil their physiological functions, located beneath the soil surface. Preferably, the term denotes the parts of a plant which are below the seed and have directly emerged from the latter, or from other roots, but not from shoots or foliage. Root grows out of root meriste which are a group of cells that are located at the distal end of the radicle and adventitious roots. The root meristem serves as the site of root proliferation, producing new cells that differentiate into specific root tissues, i.e. epidermis, cortex, endodermis, pericycle and procambium, and the root cap which protects and lubricates the root as it grows in the soil. Root hairs are produced from the epidermis after germination through interaction with the cortex.

A further aspect of the present invention relates to a method for increasing the total mass of roots of seedlings originating from seeds, said method comprising the step of contacting the seeds, the medium to be planted by the seeds or both with natamycin. In an embodiment the seeds are seeds encrusted with natamycin.

A further aspect of the present invention relates to a method for increasing the total mass of seedlings originating from seeds, said method comprising the step of contacting the seeds, the medium to be planted by the seeds or both with natamycin. In an embodiment the seeds are seeds encrusted with natamycin.

A further aspect of the present invention relates to a method for increasing the average dry mass of individual seedlings originating from seeds, said method comprising the step of contacting the seeds, the medium to be planted by the seeds or both with natamycin. In an embodiment the seeds are seeds encrusted with natamycin.

Embodiments and features described herein for an aspect of the invention also pertain to the other aspects of the invention.

EXAMPLES

Example 1

Encrusting of Rice Seeds

In this example rice seeds were encrusted with the coating compositions as shown in Table 1. Rice seeds were encrusted using the following method. Fifty grams of calcium carbonate and 2.5 or 9 grams of natamycin product were mixed to make a natamycin mixture. The natamycin product used was Delvocid®, a product comprising 50% (w/w) natamycin. Next, one kilogram of seeds were put into a pan and moistened through a spinning disc within a rotary coater. After moistening and shortly before the rice seeds started to stick to one another, the natamycin mixture was added to the seeds. After the seeds had absorbed the powder mixture and had a dry appearance, the seeds were moistened again and a mixture comprising 950 grams of calcium carbonate and 400 grams of a lignosulphonate suspension (comprising 133 grams of lignosulphonate and 267 grams of water) or a mixture comprising 950 grams of calcium carbonate and 200 grams of a polyvinylpyrrolidone solution (comprising 10 grams of polyvinylpyrrolidone and 190 grams of water) were added. After the seeds had absorbed the powder mixture, they were kept in the pan and rolled for 5-10 minutes. Thereafter, they were removed from the pan and put into a dryer for 60 minutes at a temperature of 25 to 35° C. After drying, the seeds were put through a grader to remove dust, blanks (i.e. encrustings with no seed as the centre) and doubles (i.e. encrustings with two or more seeds as the centre). After grading, the encrusted seeds were weighted and used in the following experiments.

Example 2

Germination of Encrusted Rice Seeds

In this example encrusted rice seeds (*Oryza sativa*) prepared as described in Example 1 and untreated rice seeds were subjected to germination as follows. Encrusted and untreated seeds were put into a sterile roll of paper. In total, 100 seeds were put into the sterile roll of paper. The experiment was done in fourfold (i.e. 400 seeds per treatment). The germination procedure was done according to the well known procedure from ISTA (see Handbook International Rules for Seed Testing, Edition 2011, Chapter 5, pages 5-41, published by the International Seed Testing Association, Switzerland). Each sterile paper was put into 100 ml of water and incubated at 20-30° C. in a sterile germ cabinet for 14 days. The planted seeds were subjected to the following cycle during these 14 days: 12 hours dark at 20° C. followed by 12 hours of light at 30° C.; humidity was between 98 and 100%. After 14 days, the percentage of germination was established as follows. The sterile rolls of paper with the seeds inside were removed from the sterile germination cabinet, the rolls were opened and the classification of the seedlings was done according to ISTA standards (see Handbook International Rules for Seed Testing, Edition 2011, Chapter 5, pages 5-41, published by the International Seed Testing Association, Switzerland).

The results are given in Table 2. They clearly show that a substantially higher percentage of rice seeds germinate, when they are encrusted with natamycin. The increase in germination is seen at various natamycin concentrations (e.g. 2.5 gram natamycin product per kg of seeds as well as at 9.0 gram natamycin product per kg of seeds).

Furthermore, the increase in germination is seen in coating compositions comprising different constituents, e.g. a coating composition comprising calcium carbonate and calcium lignosulphonate and a coating composition comprising calcium carbonate and polyvinylpyrrolidone.

From the above can be concluded that natamycin can be used to increase germination of seeds.

Example 3

Germination of Encrusted Rice Seeds after Storage

In this example encrusted rice seeds (*Oryza sativa*) prepared as described in Example 1 and untreated rice seeds were stored for two months. After storage, they were subjected to germination as follows. Encrusted and untreated seeds were put into a sterile roll of paper. In total, 100 seeds were put into the sterile roll of paper. The experiment was done in fourfold (i.e. 400 seeds per treatment). The germination procedure was done according to the well known procedure from ISTA (see Handbook International Rules for Seed Testing, Edition 2011, Chapter 5, pages 5-41, published by the International Seed Testing Association, Switzerland). The sterile paper was put into 100 ml of water and incubated at 20-30° C. in a sterile germ cabinet for 16 days. The planted seeds were subjected to the following cycle during these 16 days: 12 hours dark at 20° C. followed by 12 hours of light at 30° C.; humidity was between 98 and 100%. After 16 days, the percentage of germination was established as follows. The sterile rolls of paper with the seeds inside were removed from the sterile germination cabinet, the rolls were opened and the classification of the seedlings was done according to ISTA standards (see Handbook International Rules for Seed Testing, Edition 2011, Chapter 5, pages 5-41, published by the International Seed Testing Association, Switzerland).

The results are given in Table 3. They clearly show that a substantially higher percentage of stored rice seeds germinate, when they are encrusted with natamycin. The increase in germination is seen at various natamycin concentrations (e.g. 2.5 gram natamycin product per kg of seeds as well as at 9.0 gram natamycin product per kg of seeds), with 9.0 gram natamycin product per kg of seeds giving the highest increase.

Furthermore, the increase in germination is seen in coating compositions comprising different constituents, e.g. binders. However, the highest increase in germination is seen when seeds are encrusted with calcium carbonate, polyvinylpyrrolidone and natamycin.

From the above can be concluded that natamycin can be used to increase germination of seeds after the seeds have been stored. It can further be concluded that coating with calcium carbonate, polyvinylpyrrolidone and natamycin is preferred.

Example 4

Root Development of Encrusted Rice Seeds

In this example encrusted rice seeds (*Oryza sativa*) prepared as described in Example 1 and untreated rice seeds were subjected to germination essentially as described in Example 2. After 16 days, the weight of the roots of the obtained seedlings was determined. The weighing was done as follows. First, the wet roots were cut with a scalpel at the point of attachment with the cotelydons. Next, the wet roots were weighed. The weight of the roots is defined herein as total mass (dry mass and water content).

The results are given in Table 4. They clearly show that the development of roots in seedlings that originate from seeds encrusted with natamycin is better than the development of roots in seedlings that originate from untreated seeds or seeds that have been encrusted without natamycin.

Example 5

Development of Seedlings Originating from Encrusted or Untreated Rice Seeds

In this example encrusted rice seeds (*Oryza sativa*) prepared as described in Example 1 and untreated rice seeds were subjected to germination as described in Example 2. After 16 days, the seedlings were harvested and the total weight of the harvested seedlings was determined. The weight of the harvested seedlings is the total weight of the shoots and roots. The weighing was done as follows. First, the wet roots and shoots were cut with a scalpel at the point of attachment with the cotelydons. Next, the wet roots and shoots were weighed. The weight of the roots and shoots is defined herein as total mass (dry mass and water content).

The results are given in Table 5. They clearly show that the weight of the seedlings that originate from seeds encrusted with natamycin is higher than the weight of the seedlings that originate from untreated seeds or seeds that have been encrusted without natamycin.

Example 6

Dry Mass Development of Encrusted Rice Seeds

In this example encrusted rice seeds (*Oryza sativa*) prepared as described in Example 1 and untreated rice seeds were subjected to germination as described in Example 2. After 16 days, the wet roots and shoots were cut with a scalpel at the point of attachment with each of the obtained seedlings. The weight of the roots and shoots per seedling was determined and thereafter the roots and shoots were dried in an oven for 30 minutes at 130° C. After drying, the dried roots and shoots were taken out of the oven, cooled in a desiccator and the weight of the roots and shoots per individual seedling was determined again. The difference between the weight before and the weight after drying is referred to as the water content of the roots. The weight after drying is defined as dry mass.

The results are given in Table 6. They clearly show that the average dry mass of the roots and shoots per individual seedling that originates from rice seeds encrusted with natamycin is higher than the average dry mass of the roots and shoots per individual seedling that originates from untreated rice seeds or rice seeds that have been encrusted without natamycin.

Thus, more dry mass is produced per individual seedling after application of natamycin. Dry mass production can be correlated with growth stimulation, as dry mass is produced during growth of the seedling or plant.

Example 7

Germination of Rice Seeds Encrusted with Natamycin or Calcium Peroxide

Encrusted rice seeds (*Oryza sativa*) were prepared as described in Example 1, except for the fact that the following coating compositions were used for encrusting:
 Control (untreated),
 Composition A: identical to composition 4 in Table 1, applied on 1 kg of seed as described in Example 1,
 Composition B: total mixture of 1 kg calcium carbonate, 0.2 kg polyvinylpyrrolidone solution (comprising 10 grams of polyvinylpyrrolidone and 190 grams of water) and 30% (w/w) calcium peroxide was completely added to 1 kg of seed.

The encrusted and untreated rice seeds were subjected to the germination procedure described in Example 2. After 14 days, the percentage of germination was determined as described in Example 2.

The results (see Table 7) reveal that the percentage of germinated seeds was clearly higher for the seeds encrusted with natamycin. Moreover, the germination percentage of seeds encrusted with natamycin exceeded the germination percentage for seeds encrusted with calcium peroxide. Hence, natamycin outperforms calcium peroxide as growth stimulator.

Example 8

Dry Mass Development of Rice Seeds Encrusted with Natamycin or Calcium Peroxide

Encrusted rice seeds (*Oryza sativa*) were prepared as described in Example 1, except for the fact that the following coating compositions were used for encrusting:

Control (untreated),
Composition A: identical to composition 6 in Table 1, applied on 1 kg of seed as described in Example 1,
Composition B: total mixture of 1 kg calcium carbonate, 0.2 kg polyvinylpyrrolidone solution (comprising 10 grams of polyvinylpyrrolidone and 190 grams of water) and 10% (w/w) calcium peroxide was completely added to 1 kg of seed,
Composition C: total mixture of 1 kg calcium carbonate, 0.2 kg polyvinylpyrrolidone solution (comprising 10 grams of polyvinylpyrrolidone and 190 grams of water) and 30% (w/w) calcium peroxide was completely added to 1 kg of seed,
Composition D: identical to composition 3 in Table 1, applied on 1 kg of seed as described in Example 1,
Composition E: total mixture of 1 kg calcium carbonate, 0.4 kg lignosulphonate solution (comprising 133 grams of lignosulphonate and 267 grams of water) and 10% (w/w) calcium peroxide was completely added to 1 kg of seed,
Composition F: total mixture of 1 kg calcium carbonate, 0.4 kg lignosulphonate solution (comprising 133 grams of lignosulphonate and 267 grams of water) and 30% (w/w) calcium peroxide was completely added to 1 kg of seed.

The encrusted and untreated rice seeds were subjected to the germination procedure described in Example 2. After 14 days, the total dry weight of the roots and shoots per seedling was determined according to the method described in Example 6.

The results (see Table 8) clearly demonstrate that the average dry mass of the roots and shoots per individual seedling that originated from rice seeds encrusted with natamycin was higher than the average dry mass of the roots and shoots per individual seedling that originated from untreated rice seeds or rice seeds that had been encrusted with calcium peroxide. Moreover, the use of 30% calcium peroxide actually resulted in a decrease of the average dry mass of the roots and shoots per seedling when compared to untreated seeds. This higher dry mass of the seedlings of the natamycin-treated seeds was observed when either polyvinylpyrrolidone or lignosulphonate was used as individual binder in the coating composition. Hence, more dry mass is produced per individual seedling after application of natamycin, which shows that natamycin is the preferred growth stimulator compared to calcium peroxide.

Example 9

Root Development of Encrusted Corn Seeds

In this example encrusted corn seeds (*Zea mays*) were prepared essentially as described in Example 1, with the proviso that the following coating compositions were used to encrust 1 kg of corn seeds.

Composition A: 0.6 kg calcium carbonate, 0.5 kg polyvinylpyrrolidone solution (comprising 25 grams of polyvinylpyrrolidone and 475 grams of water),
Composition B: 0.6 kg calcium carbonate, 0.5 kg polyvinylpyrrolidone solution (comprising 25 grams of polyvinylpyrrolidone and 475 grams of water), 18 gram natamycin product (i.e. Delvocid®, a product comprising 50% (w/w) natamycin).

Encrusted and untreated seeds were put into a sterile roll of paper. In total, 25 seeds were put into the sterile roll of paper. The experiment was done in eightfold (i.e. 200 seeds per treatment). The germination procedure was done according to the well known procedure from ISTA (see Handbook International Rules for Seed Testing, Edition 2011, Chapter 5, pages 5-46, published by the International Seed Testing Association, Switzerland). Each sterile paper was put into 75 ml of water and incubated at 20-30° C. in a sterile germ cabinet for 14 days. The planted seeds were subjected to the following cycle during these 14 days: 12 hours dark at 20° C. followed by 12 hours of light at 30° C.; humidity was between 98 and 100%. After 14 days, the sterile rolls of paper with the seeds inside were removed from the germination cabinet, the rolls were opened and the average dry mass of the roots per individual seedling was determined as follows. The wet roots were cut with a scalpel at the point of attachment with each of the obtained seedlings. The weight of the roots per seedling was determined and thereafter the roots were dried in an oven for 30 minutes at 130° C. After drying, the dried roots were taken out of the oven, cooled in a desiccator and the weight of the roots per individual seedling was determined again. The difference between the weight before and the weight after drying is referred to as the water content of the roots. The weight after drying is defined as dry mass.

The results are given in Table 9. They clearly show that the average dry mass of the roots per individual seedling that originates from corn seeds encrusted with natamycin is higher than the average dry mass of the roots per individual seedling that originates from corn seeds that have been encrusted without natamycin.

The example was repeated with compositions wherein the pelleting powder Y5 (comprising about 3% (w/w) sulfates, about 30% (w/w) calcium, about 30% (w/w) carbonates and about 35% (w/w) silica) was used instead of calcium carbonate. The results were comparable to the results with calcium carbonate in that the average dry mass of the roots per individual seedling that originates from corn seeds encrusted with natamycin is higher than the average dry mass of the roots per individual seedling that originates from corn seeds that have been encrusted without natamycin.

Hence, more dry mass is produced per individual seedling after application of natamycin. Dry mass production can be correlated with growth stimulation, as dry mass is produced during growth of the seedling or plant.

Example 10

Germination of Coated Onion Seeds

In this example onion seeds (*Allium cepa*) were untreated or coated with one of the following compositions.
Composition A: 1.5 gram polyvinylpyrrolidone, 3 gram natamycin product (i.e. Delvocid®, a product comprising 50% (w/w) natamycin),
Composition B: 1.5 gram polyvinylpyrrolidone, 6 gram natamycin product (i.e. Delvocid®, a product comprising 50% (w/w) natamycin),
Composition C: 1.5 gram polyvinylpyrrolidone, 9 gram natamycin product (i.e. Delvocid®, a product comprising 50% (w/w) natamycin),
Composition D: 1.5 gram polyvinylpyrrolidone, 15 gram natamycin product (i.e. Delvocid®, a product comprising 50% (w/w) natamycin)

Coating was done according to the following method. The above-mentioned compositions were dissolved in 30 ml water to prepare aqueous solutions. Next, one kilogram of seeds was put into a rotary coater and the respective solutions were applied to the seeds. The seeds were rotated for 45 seconds with the respective solutions. The solutions were evenly spread over the seeds through the spinning disc of the rotary coater. Thereafter, the seeds were removed from the rotary coater and put into a dryer for 15 minutes at a temperature of 25 to 40° C.

Next, the coated onion seeds and the untreated onion seeds were subjected to germination. For this, coated and untreated seeds were put into a sterile roll of paper. In total, 100 seeds were put into the sterile roll of paper. The experiment was done in fourfold (i.e. 400 seeds per treatment). The germination procedure was done according to the well known procedure from ISTA (see Handbook International Rules for Seed Testing, Edition 2011, Chapter 5, pages 5-32, published by the International Seed Testing Association, Switzerland). Each sterile paper was put into 50 ml of water and incubated at 15-20° C. in a sterile germ cabinet for 12 days. The planted seeds were subjected to the following cycle during these 12 days: 16 hours dark at 20° C. followed by 8 hours of light at 20° C.; alternatively, 16 hours dark at 15° C. followed by 8 hours of light at 20° C. can be used; humidity was between 98 and 100%. After 12 days, the percentage of germination was established as follows. The sterile rolls of paper with the seeds inside were removed from the germination cabinet, the rolls were opened and the classification of the seedlings was done according to ISTA standards (see Handbook International Rules for Seed Testing, Edition 2011, Chapter 5, pages 5-32, published by the International Seed Testing Association, Switzerland)

The results are given in Table 10. They clearly show that a substantially higher percentage of onion seeds germinate, when they are coated with natamycin. The increase in germination is seen at various natamycin concentrations.

From the above can be concluded that natamycin can be used to improve the germination of seeds.

Example 11

Germination of Coated Watermelon Seeds

Watermelon (*Citrullus lanatus*) seeds were untreated or coated with a composition comprising 1.5 gram polyvinylpyrrolidone and 9 gram natamycin product (i.e. Delvocid®, a product comprising 50% (w/w) natamycin) per kg of seed. This composition was applied as described in Example 10.

Subsequently, the seeds were germinated in trays of sterile, buffered (i.e. with calcium nitrate to pH of 6.7) cocopeat, which is a stable growth medium commonly used and accepted for e.g. simulation of seed germination in the horticultural industry. The 50 seeds planted per treatment were subjected to an ambient temperature of minimally 1.4° C. during night time and maximally 26.9° C. during day time (average temperature 13.6° C.) for 19 days and continuously irrigated to field capacity. The average relative humidity during the trial was 72%. During the trial, the trays with cocopeat were irrigated 3 to 5 times per day. The trays were perforated at the bottom leading to direct removal of excess water. This way, the cocopeat could be kept at field capacity. After 15, 17 and 19 days, the germination percentage was determined according to ISTA standards (see Handbook International Rules for Seed Testing, Edition 2011, Chapter 5, pages 5-32, published by the International Seed Testing Association, Switzerland).

The results in Table 11 show that a significantly higher percentage of watermelon seeds germinated when coated with natamycin. After 15, 17 and 19 days of incubation, the germination percentage of the seeds coated with natamycin exceeded the germination percentage of the untreated seeds with 18, 34 and 38%, respectively.

Thus, application of natamycin on watermelon seeds clearly stimulates germination of these seeds.

Example 12

Germination of Drum Primed, Encrusted Tomato Seeds

Tomato (*Solanum lycopersicum*) seeds were primed (i.e. brought to same germination level) using drum priming. Subsequently, the primed tomato seeds were either not treated further or encrusted with composition 6 of Table 1 according to the method as described in Example 1. Subsequently, 100 seeds per treatment were subjected to the germination procedure as described in Example 11. After 10 and 19 days, the germination percentage was determined using the ISTA method described in Example 11.

The results in Table 12 prove that a significantly higher percentage of primed tomato seeds germinated when encrusted with natamycin. After both 10 and 19 days of incubation, the germination percentage of the primed tomato seeds encrusted with natamycin exceeded the germination percentage of the control seeds with 10%.

From these results it can be concluded that application of natamycin on tomato seeds leads to enhanced seed germination.

Example 13

Germination of Osmo Primed, Coated Eggplant Seeds

Eggplant (*Solanum melongena*) seeds were primed (i.e. brought to same germination level) using osmo priming. Subsequently, the primed eggplant seeds were either not treated further or coated with a composition comprising 1.5 gram polyvinylpyrrolidone and 9 gram natamycin product (i.e. Delvocid®, a product comprising 50% (w/w) natamycin) per kg of seed. This composition was applied as described in Example 10. The uncoated and coated primed seeds were germinated using the ISTA germination procedure described in Example 10, except for the fact that each treatment consisted of four replicates of 50 seeds each (i.e. in total 200 seeds per treatment). Furthermore, the planted seeds were subjected to the following cycle for 14 days: 16 hours in the dark at 20° C. followed by 8 hours of light at 30° C.; humidity was between 98 and 100%. After 14 days, the percentage of germination was assessed as described in Example 10.

The results in Table 13 clearly demonstrate that a higher percentage of osmo primed eggplant seeds germinated when coated with natamycin. Hence, application of natamycin on eggplant seeds stimulates their germination.

TABLE 1

Coating compositions for encrusting 1 kg of rice seeds.

| Composition | Calcium carbonate (kg) | Lignosulphonate (kg) | Polyvinylpyrrolidone (kg) | Natamycin product (g/kg seeds) |
|---|---|---|---|---|
| 1 | 1 | 0.133 | 0 | 0 |
| 2 | 1 | 0 | 0.01 | 0 |
| 3 | 1 | 0.133 | 0 | 2.5 |
| 4 | 1 | 0 | 0.01 | 2.5 |
| 5 | 1 | 0.133 | 0 | 9 |
| 6 | 1 | 0 | 0.01 | 9 |

TABLE 2

Percentage of germination after 14 days of incubation of encrusted and untreated rice seeds.

| Composition | Percentage of germination (%) |
|---|---|
| Control (untreated) | 82 |
| 1 | 89 |
| 2 | 86 |
| 3 | 94 |
| 4 | 94 |
| 5 | 94 |
| 6 | 95 |

TABLE 3

Percentage of germination after 16 days of incubation of stored encrusted and untreated rice seeds.

| Composition | Percentage of germination (%) |
|---|---|
| Control (untreated) | 64 |
| 1 | 72 |
| 2 | 78 |
| 3 | 71 |
| 4 | 84 |
| 5 | 80 |
| 6 | 91 |

TABLE 4

Total mass (dry mass and water content) of the roots of seedlings originating from encrusted and untreated rice seeds.

| Composition | Total mass of roots (in gram) |
|---|---|
| Control (untreated) | 2.16 |
| 1 | 2.63 |
| 2 | 3.06 |
| 5 | 3.21 |
| 6 | 3.29 |

TABLE 5

Total mass (dry mass and water content) of seedlings originating from encrusted and untreated rice seeds.

| Composition | Total mass of seedlings (in gram) |
|---|---|
| Control (untreated) | 14.19 |
| 1 | 17.65 |
| 2 | 19.10 |
| 5 | 20.18 |
| 6 | 20.37 |

TABLE 6

Average dry mass of individual seedlings originating from encrusted and untreated rice seeds.

| Composition | Average dry mass weight per seedling (in gram) | Percentage increase in average dry mass compared to untreated seeds (%) |
|---|---|---|
| Control (untreated) | 0.0065 | — |
| 1 | 0.0084 | 28 |
| 2 | 0.0089 | 36 |
| 3 | 0.0093 | 42 |
| 4 | 0.0098 | 50 |

TABLE 7

Percentage of germination after 14 days of incubation of rice seeds encrusted with natamycin or calcium peroxide.

| Composition | Percentage of germination (%) |
|---|---|
| Control (untreated) | 70 |
| A (natamycin) | 76 |
| B (calcium peroxide) | 72 |

TABLE 8

Average dry mass of individual seedlings originating from rice seeds encrusted with natamycin or calcium peroxide.

| Composition | Average dry mass weight per seedling (in gram) | Percentage increase in average dry mass compared to untreated seeds (%) |
|---|---|---|
| Control (untreated) | 0.0041 | — |
| A (natamycin) | 0.0054 | 33 |
| B (calcium peroxide) | 0.0043 | 7 |
| C (calcium peroxide) | 0.0033 | −19 |
| D (natamycin) | 0.0048 | 18 |
| E (calcium peroxide) | 0.0042 | 3 |
| F (calcium peroxide) | 0.0024 | −40 |

TABLE 9

Average dry mass of the roots per individual seedling originating from encrusted and untreated corn seeds.

| Composition | Percentage increase in average dry mass compared to untreated seeds (%) |
|---|---|
| Control (untreated) | — |
| A | 4 |
| B | 17 |

TABLE 10

Percentage of germination after 12 days of incubation of coated and untreated onion seeds.

| Composition | Percentage of germination (%) |
|---|---|
| Control (untreated) | 73 |
| A | 79 |
| B | 80 |
| C | 85 |
| D | 85 |

TABLE 11

Percentage of germination after 15, 17 and 19 days of incubation of coated and untreated watermelon seeds.

| | Percentage of germination (%) during incubation (days) | | |
|---|---|---|---|
| Composition | 15 days | 17 days | 19 days |
| Control (untreated) | 12 | 16 | 22 |
| Natamycin-coated | 30 | 50 | 60 |

TABLE 12

Percentage of germination after 10 and 19 days of incubation of drum primed, (un)encrusted tomato seeds.

| Composition | Percentage of germination (%) during incubation (days) | |
|---|---|---|
| | 10 days | 19 days |
| Control (drum primed) | 70 | 75 |
| Drum primed + natamycin-coated | 80 | 85 |

TABLE 13

Percentage of germination after 14 days of incubation of osmo primed, (un) coated eggplant seeds.

| Composition | Percentage of germination (%) |
|---|---|
| Control (osmo primed) | 41 |
| Osmo primed + natamycin-coated | 45 |

The invention claimed is:

1. A method for improving seed germination, said method comprising coating the seed with a composition comprising an effective amount of natamycin and a filler, a binder or both to produce a coated seed, wherein the effective amount of natamycin improves germination of the coated seed at least 5% as measured by percent of germination after 14 days.

2. A method according to claim 1, wherein the filler is selected from the group consisting of a carbonate, wood flour, diatomaceous earth and a combination thereof.

3. A method according to claim 1, wherein the binder is lignosulphonate, polyvinylpyrrolidone or a combination thereof.

4. A method according to claim 1, wherein natamycin is present in an amount of 10 grams to 4000 grams of natamycin per 100 kg of seeds.

5. The method according to claim 1, wherein the effective amount of natamycin improves germination of the coated seed at least 10% as measured by percent of germination after 14 days.

6. A seed treatment composition comprising a filler, a binder and an effective amount of natamycin, wherein the filler is selected from the group consisting of a carbonate, wood flour, diatomaceous earth and a combination thereof and wherein the natamycin in said composition improves seed germination at least 5% as measured by percent of germination after 14 days.

7. A seed treatment composition according to claim 6, wherein the binder is lignosulphonate, polyvinylpyrrolidone or a combination thereof.

8. A seed treatment composition according to claim 6, wherein natamycin is present in an amount of from 0.05 to 50% of the total weight of the composition.

9. The seed treatment composition according to claim 6, wherein the effective amount of natamycin in said composition improves seed germination at least 10% as measured by percent of germination after 14 days.

10. A seed comprising a composition according to claim 6.

11. A medium for growing a plant comprising a composition according to claim 6.

12. A coated seed comprising a filler, a binder and an effective amount of natamycin, wherein the filler is selected from the group consisting of a carbonate, wood flour, diatomaceous earth and a combination thereof and wherein the effective amount of natamycin on the coated seed improves seed germination at least 5% as measured by percent of germination after 14 days.

13. The coated seed of claim 12, wherein the effective amount of natamycin on the coated seed improves seed germination at least 10% as measured by percent of germination after 14 days.

14. The coated seed of claim 12, wherein the coated seed is selected from the group consisting of rice seed, corn seed, onion seed, watermelon seed, tomato seed and eggplant seed.

15. A method for growing a plant, said method comprising:
   a) sowing a seed according to claim 12, and
   b) allowing the plant to grow from the seed.

* * * * *